United States Patent [19]

Braquet et al.

[11] Patent Number: 5,081,148

[45] Date of Patent: Jan. 14, 1992

[54] BLOCKING AGENTS OF EDRF EFFECT OR FORMATION FOR THE TREATMENT OF SHOCK

[75] Inventors: Pierre Braquet, Garches; Pierre-Etienne Chabrier de Lassauniere, Paris; Jean-Michel Guillon, Bourg la Reine; Michel Auguet, Palaiseau, all of France

[73] Assignee: Societe de Conseils de Recherches et D'Applications Scientifiques (S.C.R.A.S.), France

[21] Appl. No.: 630,273

[22] Filed: Dec. 19, 1990

[30] Foreign Application Priority Data

Dec. 22, 1989 [GB] United Kingdom ............... 8929076

[51] Int. Cl.$^5$ .................... A61K 31/22; A61K 31/40; A61K 31/215; A61K 31/615
[52] U.S. Cl. .................... 514/162; 514/529; 514/551; 514/420; 514/921
[58] Field of Search ............... 514/529, 551, 921, 162, 514/420

[56] References Cited

PUBLICATIONS

BIOSIS #88127938, Aisaka et al L-Arginine availability determines the duration of acetylcholine-induced systemic vasodilation in vivo.

Vallance et al. BIOSIS #89074491, Nitric oxide synthesized from L-arginine mediates endothelium dependent dilation in human vein in-vivo.

Primary Examiner—Stanley J. Friedman
Attorney, Agent, or Firm—Lucas & Just

[57] ABSTRACT

The invention relates to a therapeutical composition of matter for the treatment by perfusion of shock states comprising as an essential ingredient therein, an effective amount either, of a compound of the formula:

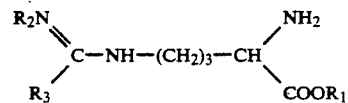

wherein
  $R_1$ and $R_4$ stant for H or $CH_3$ or $C_2H_5$,
  $R_2$ stands for H or $NO_2$ and
  $R_3$ stands for $NHR_4$ or $CH_3$ or $C_2H_5$ alone or of a mixture of said compound with a cyclooxygenase blocker.

6 Claims, No Drawings

BLOCKING AGENTS OF EDRF EFFECT OR FORMATION FOR THE TREATMENT OF SHOCK

The present invention relates to new blocking agents of endothelium derived relaxing factor (EDRF) for the treatment of various shocks such as, for example, stresses, septic shocks or traumatic shocks.

Sepsis and endotoxemia are still the major causes of death in surgical intensive care units despite the use of large amounts and specific antibiotics, careful monitoring and operative interventions. Non-surviving patients tend to have a lower peripheral vascular resistance described as "unrelenting hypotension". Indeed, patients present a deep vasodilatation especially in the preterminal phase and die of peripheral vascular failure more than of cardiac failure. Moreover, the persistant vasodilatation in these patients is only temporarily responsive to infused catecholamines (or other vasoconstrictor agents) and cannot usually be restored due to a "vascular hyporesponsiveness" which is the major factor contributing to mortality.

The present invention relates to the treatment of vascular hyporesponsiveness in various shock states such as sepsis, endotoxemia and other diseases leading to persistant and deep systemic vasodilatation. The treatment includes the administration of an effective amount of a blocking agent of the effect or the production of endothelium derived relaxing factor (EDRF) or nitric oxide, like factor.

According to the invention it has been found that blocking agents of the effect or of the generation of EDRF, for example, derivatives of L-arginine such as L-N-monomethyl arginine or L-NMMA L-iminoethylornithine or L-NIO and L-nitroarginine methyl ester or L-NAME, for instance, are able to restore depressed response to catecholamines and to effectively inhibit vascular hyporeactivity.

These derivatives are the L-isomers of the compounds of the following formula:

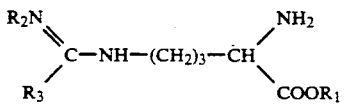

wherein $R_1$ and $R_4$ stand for H or $CH_3$ or $C_2H_5$, $R_2$ stands for H or $NO_2$ and $R_3$ stands for $NHR_4$ or $CH_3$ or $C_2H_5$ with the proviso that $R_1$, $R_2$ and $R_4$ cannot all be H.

Accordingly, the invention relates to therapeutic compositions of matter containing an effective amount of at least one of the above-mentioned compounds associated with any compatible carrier and/or diluents for the administration by injection.

The state of the art may be illustrated by European Patent Application No. 86117895.2 dated 22.12.86 which describes cytoprotective agents and cites (D) N-methyl arginine. However, it should be noted that, first, this compound is deprived of any activity in the field of the present invention and, secondly, that the compounds of the present invention do not appear to have any cytoprotective action.

For the experimental demonstration, a large amount of evidence has previously shown that animal models of shock in vivo and in vitro well mimic the human vascular hyporesponsiveness to pressor neurotransmitters or hormones (Wichterman K. A., Baue A. E., Chaudry T. H. Sepsis and septic shock. A review of laboratory models and a proposal. J. of Surgical Res. 29, 189-201 (1980), Parrat J. R. Alteration in vascular reactivity in sepsis and endotoxemia. In: Vincent J. L. (Ed.) Update in intensive care and emergency medicine. Springer vol. 8, 299-308, 1989). This abnormal vascular responsiveness and the effect of blocking agents of EDRF can be well demonstrated in vascular tissues removed from animals in shock.

For the compounds of the invention, this was evidenced by the following experiments:

Sprague Dawley rats (220-330 g) received a 10 mg/kg ip injection of Escherichia Coli endotoxin (0114B4 Sigma). After 3 hours, rats were sacrificed by cervical dislocation and the thoracic aorta removed and cleaned of the surrounding tissue. Rings 2 mm wide were suspended under a tension of 2 g at 37° C. in organ bath containing 10 ml of Krebs Henseleit physiological solution and gassed with 95% $O_2$/5% $CO_2$. Contractile responses were measured using force displacement transducers (Auguet M., Delaflotte S., P. E. Chabrier, P. Braquet Comparative effects of endotelin and phorbol 12-13 dibutyrate in rat aorta. Life Sci. 45, 21, 2051-2059, 1989).

In some experiments, the endothelium was gently disrupted ($-E$). Phenylephrine (PE) induced contraction was stable over the time in control rings of animals receiving saline solution (0.9% NaCl) with (E+) or without (E−) endothelium. The arginine derivative (10, 30 or 100 μM) had no significant effect per se.

Adversely, rings from animals treated with endotoxin showed, despite a similar contractile effect to PE, a loss of tonicity within the time referred as vascular hyporeactivity. This phenomenon was accentuated with intact endothelium (E+). The compounds of the invention (at 10, 30 or 100 μM) were able to reverse the loss of tonicity indicating that these compounds could inhibit the vascular hyporesponsiveness in preparations with or without endothelium.

The effect of the compounds of the invention was specific to the inhibition of EDRF generation whereas L-arginine, the natural precursor of nitric oxide, enhanced the loss of tonicity in endotoxin treated preparation.

In some experiments, the compounds of the invention were introduced in the bath 105 minutes after PE when the tissue had completely its tonicity. Under these conditions, the compounds of the invention, alone, were able to curatively and totally restore the contraction and therefore contribute extensively to vascular hyporesponsiveness to vasoconstrictor agents in shock. It has also been found that the action of the compounds of the invention might be strongly increased when associated to blockers of cyclooxygenase such as aspirin and indomethacin for instance. This was evidenced by the following in vivo experimentation.

Male Sprague Dawley rats (280-320 g) were pithed and perfused continuously with endotoxin (EDTX, Escherichia Coli lipopolysaccharide OIII: B4; 300 μg/kg/h) for 60 min. This resulted in a systemic hypotension (decrease of DBP (diastolic blood pressure) of 40%, a vascular hyporeactivity to stimulation of pressor agents accompanied by hemoconcentration and leukocytopenia. The vascular reactivity was measured by constructing dose-response curves to methoxamine (an $\alpha_1$-agonist) in a cumulative fashion and by calculating the ED$_{50}$ (Effective dose 50%). The ED$_{50}$ values for methoxamine were 79±9 µg/kg and 278±34 µ/kg for control and EDTX-treated rats repectively (n=24 animals). Animals were perfused with the drugs for 60 min. The number of rats in each group was 5 or 6. Results are presented in the following table. A 60 min perfusion of endotoxin lipopolysaccharide (300 µg/kg/h) to pithed rats led to hypotension and impaired the vascular reactivity to pressor agents as observed in septic and endotoxinic shock in human. This vascular hyporeactivity can be inhibited in a dose dependent manner by blockers of EDRF such as L-NMMA, L-NAME or L-NIO confirming the in vitro results. Their effects on blood pressure are however less marked. Association of blockers of cyclooxygenase (aspirin, indomethacin for instance . . .) and blockers of EDRF results on a highly significative synergistic protective effect in both vascular hyperactivity and decrease of blood pressure induced by shock.

Accordingly, this invention relates also to therapeutic compositions of matter wherein the compounds hereabove described are associated with blockers of cyclooxygenase.

It should be noted that when associating both kinds of compounds the resulting activity is far more important than the one corresponding to a mere addition of the activity of both components.

TOXICITY

An acute toxicity study of the compounds of this invention has been conducted on rats and mice but no death was noticed at the maximum administrable dosage.

POSOLOGY

For the treatment of shock the usual posology comprises the administration by perfusion of 10 to 500 mg/hour, dissolved or suspended in a serum, of the selected compound of the invention, when used alone. The duration of treatment has to be determined in each case in relationship with a sufficient recovery of the patient. In case of co-administration of one of the compounds according to the invention with a blocker of cyclooxygenase, the dose for one hour of perfusion contains 10 to 100 mg of the selected compound according to the invention, associated with, 0.1 to 1 mg, if indomethacin is used, or 2 to 200 mg, if aspirin is used, or the corresponding amounts of other blockers of cyclooxygenase.

As to the obtention of the compounds of this invention, they can be easily obtained according to the indications given in the following references:

1- "Arginine derivatives methylated in their guanidine group." Bajusz, Sandor L, published on Apr. 27th 1974 and filed on Feb. 22nd 1972,
2- "NG-Alkylarginine purification." Kikumoto, Ryoji L, published on June 29th 1976 and filed on Dec. 23rd 1974,
3- European Patent N° 230 037 "Preparation of guanidino-alkylcarboxylic acid esters as cytoprotective agents for the treatment of ischemia and hypoxia", published on July 29th 1987 and filed on Dec. 23rd 1985,
4- "NG-Methylated arginines. Convenient preparation of NG-methylarginine." Corbin, James L, Anal. Biochem. 1974,
5- "Preparation and characterization of NG-mono-di-and trimethylated arginines." Patthy A, Bajusz L, Acta Biochim.Biophys.Acad.Sci.Hung 1977,
6- "Synthesis of guanidine-N-alkylarginine by the use of polymeric pseudouress" Pundak, Shlomo, Wilcheck Meir, J. Org.Chem. 1981,
7- "Carrier mediated synthesis of NG-alkyl arginines and their peptides." Wilcheck M, Pundak, S Pept. Struct.Biol. Proc.Am.Pept.Symp. 6th 1979,
8- "A convenient synthesis of NG-mono methyl-L-arginine." Abou-Gharbia L, Labelled Compd.Radiopharm. 1981.

| | Dose in mg/kg/h | Vascular reactivity (methoxamine) ED$_{50}$ (µg/kg) |
|---|---|---|
| Control | | 79 ± 9 |
| EDTX treated animals | | 278 ± 34 |
| L-NMMA | 12.5 | 246 ± 31 |
| L-NMMA | 50 | 189 ± 15 |
| L-NMMA | 100 | 130 ± 8 |
| L-NAME | 10 | 238 ± 26 |
| L-NAME | 30 | 121 ± 11 |
| L-NAME | 100 | 105 ± 7 |
| L-NIO | 50 | 200 ± 10 |
| L-NIO | 400 | 138 ± 12 |
| ASPIRIN | 3.75 | 248 ± 24 |
| ASPIRIN | 150 | 136 ± 29 |
| ASPIRIN | 300 | 107 ± 10 |
| INDOMETHACIN | 0.5 | 254 ± 22 |
| INDOMETHACIN | 20 | 128 ± 16 |
| ASPIRIN + L-NMMA | 3.75 50 | 76 ± 15 |
| ASPIRIN + L-NAME | 3.75 30 | 79 ± 12 |
| ASPIRIN + L-NMMA | 150 50 | 58 ± 5 |
| ASPIRIN + L-NAME | 150 30 | 62 ± 4 |
| INDOMETHACIN + L-NMMA | 0.5 50 | 80 ± 8 |
| INDOMETHACIN + L-NAME | 0.5 30 | 80 ± 8 |
| | | 74 ± 7 |

We claim:

1. A therapeutical composition of matter for the treatment by perfusion of shock states comprising as an essential ingredient therein an effective amount of a compound of the formula:

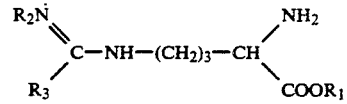

wherein
R$_1$ and R$_4$ stand for H or CH$_3$ or C$_2$H$_5$,
R$_2$ stands for H or NO$_2$ and
R$_3$ stands for NHR$_4$ or CH$_3$ or C$_2$H$_5$
with the proviso that R$_1$, R$_2$ and R$_4$ cannot all be H, together with a cyclooxygenase blocker in an amount sufficient to block cyclooxygenase.

2. The composition of claim 3 containing, as an effective amount, for a one hour perfusion, from 10 to 500 mg of the selected compound.

3. A therapeutical composition of matter for the treatment by perfusion of shock states comprising as an essential ingredient therein an effective amount of a mixture of a compound of the formula:

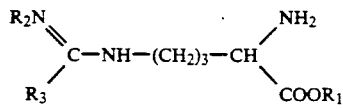

wherein $R_1$ and $R_4$ stand for H or $CH_3$ or $C_2H_5$, $R_2$ stands for H or $NO_2$ and $R_3$ stands for $NHR_4$ or $CH_3$ or $C_2H_5$ with the proviso that $R_1$, $R_2$ and $R_4$ cannot all be H, with a cyclooxygenase blocker selected from within indomethacin and aspirin.

4. The composition of claim 2 containing, as an effective amount of the mixture, for a one hour perfusion, from 10 to 100 mg of the selected compound associated with 0.1 to 1 mg of indomethacin, or with 2 to 200 mg of aspirin or with the corresponding amounts of other blockers of cyclooxygenase.

5. The composition of claim 3 wherein the cyclooxygenase blocker is indomethacin in the amount of 0.1 to 1 mg.

6. The composition of claim 3 wherein the cyclooxygenase blocker is aspirin in the amount of 2 to 200 mg.

* * * * *